(12) United States Patent
Bristow

(10) Patent No.: US 9,693,558 B2
(45) Date of Patent: Jul. 4, 2017

(54) PROCESS FOR PREPARING A NOVEL CRYSTALLINE FORM OF MESOSULFURON-METHYL AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/957,768

(22) Filed: Dec. 3, 2015

(65) Prior Publication Data

US 2017/0156330 A1     Jun. 8, 2017

(51) Int. Cl.
| A01N 47/36 | (2006.01) |
| A01N 25/12 | (2006.01) |
| A01N 25/14 | (2006.01) |
| C07D 239/52 | (2006.01) |

(52) U.S. Cl.
CPC ........... *A01N 47/36* (2013.01); *C07D 239/52* (2013.01)

(58) Field of Classification Search
CPC .............................. A01N 47/36; C07D 239/52
See application file for complete search history.

(56) References Cited

U.S. PATENT DOCUMENTS

| 5,550,238 A * | 8/1996 | Chiang ................ C07D 521/00 544/206 |
| 5,648,315 A * | 7/1997 | Lorenz .................. A01N 47/36 504/214 |
| 6,420,381 B1 * | 7/2002 | Muraoka .............. C07D 471/04 514/300 |
| 2002/0062029 A1 | 5/2002 | Lorenz et al. |
| 2015/0031877 A1 * | 1/2015 | Hiratsuka .............. A01N 43/84 544/105 |

FOREIGN PATENT DOCUMENTS

CN     103333120     * 10/2013

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
HCAPLUS abstract 2013:1544424; abstracting CN 103333120 (Oct. 2013).*
Derwent abstract, accession No. 2013-W87973; abstracting CN 103333120 (Oct. 2013).*
HCAPLUS abstract 1999:261209 (1999).*
Roberts, R.M. et al. Modern Experimental Organic Chemistry. Holt, Rinehart and Winston, New York, 1979, pp. 49-58.*
International Search Report and Written Opinion regarding PCT/CN2016/098749 dated Dec. 1, 2016.

* cited by examiner

*Primary Examiner* — John Pak
(74) *Attorney, Agent, or Firm* — Dickinson Wright PLLC

(57) ABSTRACT

A crystalline form of mesosulfuron-methyl of formula (I), the crystal preparation process, the analyses of the crystal through various analytical methods and using the crystal to prepare stable agrochemical formulation. The invention also describes the use of various solvents towards the crystalline form preparation conditions.

12 Claims, 4 Drawing Sheets

PROCESS FOR PREPARING A NOVEL CRYSTALLINE FORM OF MESOSULFURON-METHYL AND USE OF THE SAME

BACKGROUND

Field

The present disclosure relates to a crystalline form of methyl 2-[(4,6-dimethoxypyrimidin-2-ylcarbamoyl)sulfamoyl]-α-(methanesulfonamido)-p-toluate (mesosulfuron-methyl), to its preparation processes and to its use in agrochemical preparations.

Description of Related Art

Mesosulfuron-methyl, i.e., methyl 2-[(4,6-dimethoxypyrimidin-2-ylcarbamoyl)sulfamoyl]-α-(methanesulfonamido)-p-toluate, is a potent herbicide having high selectivity, high efficiency, low toxicity and other desirable attributes. Mesosulfuron-methyl has molecular formula of $C_{17}H_{21}N_5O_9S_2$. Its chemical structure is:

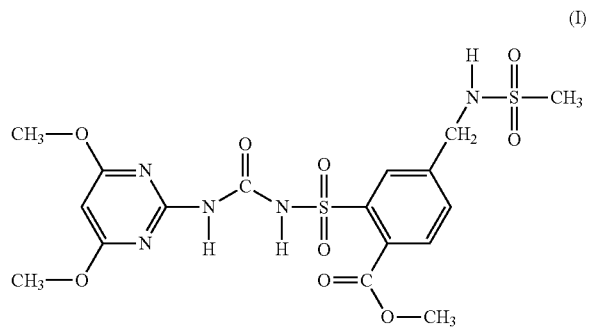

(I)

It is used post-emergence on crops, such as wheat and cereals, against a variety of annual and perennial grasses and broadleaved weeds. It is rather less toxic towards algae and is of generally low toxicity towards most wildlife.

The commercially available mesosulfuron-methyl, which is usually manufactured by the process described in U.S. Pat. No. 5,648,315 is present in an amorphous state. It has been found that mesosulfuron-methyl in the amorphous state is highly unstable. It will generally undergo significant hydrolysis when dissolved or dispersed in water. Furthermore, hydrolysis can occur during storage, particularly where the compound is exposed to moisture. As a result, the stability of mesosulfuron-methyl is of great concern with respect to providing commercially available formulations. Therefore, there is a need to provide a novel form of mesosulfuron-methyl with increased stability in formulations.

SUMMARY

Accordingly, in one embodiment, the invention provides a novel crystalline form of mesosulfuron-methyl, termed "crystalline modification I", and a process for its preparation, as well as agrochemical compositions containing it, and methods for using it in agrochemical applications, such as methods for applying it to plants, plant parts and surroundings. The novel crystalline modification I has been found to have increased stability relative to the amorphous form.

Accordingly, in another embodiment, the invention also provides compositions for controlling undesirable plant growth, such as weeds, comprising the crystalline modification I of mesosulfuron-methyl on its own, as a mixture with auxiliaries and carriers, and as a mixture with other active compounds. The use of the crystalline modification I of mesosulfuron-methyl in the control of undesired plant growth and a method for the same are also provided by an embodiment of the invention.

BRIEF DESCRIPTION OF DRAWINGS

Various aspects of the invention can be more clearly understood by reference to the drawings, which are described below, and are intended to be illustrative, not limiting, of the invention.

DETAILED DESCRIPTION OF SPECIFIC EMBODIMENTS

Figure 1:
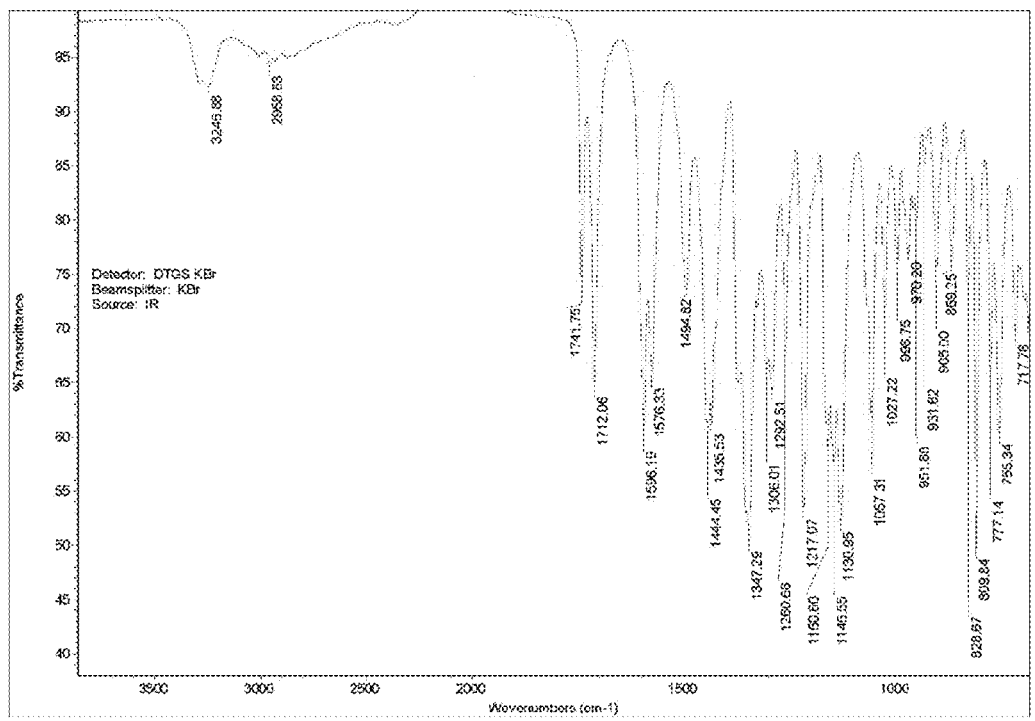
FIG. 1 is an infrared (IR) spectrum of crystalline modification I of mesosulfuron-methyl, according to an embodiment of the invention.

The embodiments and aspects of the invention disclosed herein can be more clearly understood by the following detailed description of specific embodiments and examples, which are intended to illustrate, but not limit, the scope of the appended claims.

It has been found that the crystalline modification I of mesosulfuron-methyl has a significant increase in its stability, which significantly reduces or avoids the hydrolysis problems encountered in current commercially available formulations, which contain the amorphous form of mesosulfuron-methyl. In addition, it has been found that the crystalline modification I of mesosulfuron-methyl is easier to comminute or grind into particles, compared to amorphous mesosulfuron-methyl prepared in accordance with the disclosure of U.S. Pat. No. 5,648,315, which is incorporated herein by reference in its entirety for all purposes. This allows the preparation of commercial formulations such as suspension concentrates (SC), oil-based suspension concentrates (OD), water-dispersible granules (WG) and water-soluble granules (SG). Hence, it is possible to prepare any formulations of mesosulfuron-methyl in crystalline modification I, as will be disclosed in more detail hereinafter.

By virtue of its high stability, the crystalline modification I of mesosulfuron-methyl disclosed herein is highly suitable for preparing compositions for controlling undesirable weeds.

According to an embodiment of the invention, a crystalline modification I of mesosulfuron-methyl is provided, exhibiting at least 3 of the following reflexes as 2θ values in an X-ray powder diffractogram recorded using Cu-Kα radiation at 25° C.:

$$2\theta = 5.41 \pm 0.2 \quad (1)$$

$$2\theta = 10.26 \pm 0.2 \quad (2)$$

$$2\theta = 10.88 \pm 0.2 \quad (3)$$

$$2\theta = 12.14 \pm 0.2 \quad (4)$$

$$2\theta = 16.38 \pm 0.2 \quad (5)$$

$2\theta=18.87\pm0.2$ (6)

$2\theta=19.47\pm0.2$ (7)

$2\theta=20.82\pm0.2$ (8)

$2\theta=21.88\pm0.2$ (9)

$2\theta=22.55\pm0.2$ (10)

$2\theta=22.96\pm0.2$ (11)

$2\theta=23.22\pm0.2$ (12)

$2\theta=24.10\pm0.2$ (13)

$2\theta=24.50\pm0.2$ (14)

$2\theta=26.35\pm0.2$ (15)

Figure 2:
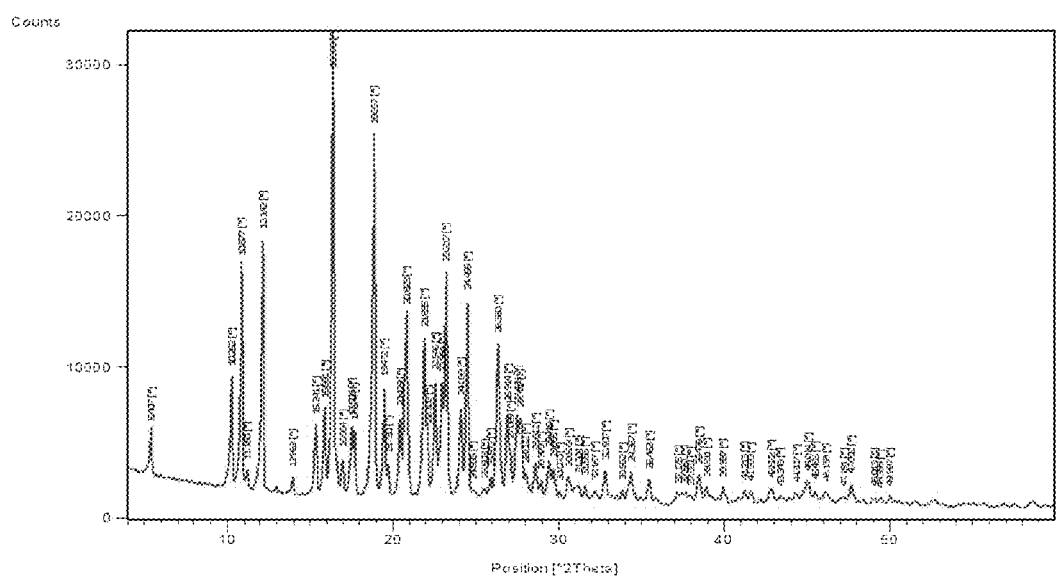
FIG. 2 is a X-ray powder diffractogram (XRD) of crystalline modification I of mesosulfuron-methyl, according to an embodiment of the invention.

More particularly, the crystalline modification I of an embodiment of mesosulfuron-methyl of the invention is characterized by an X-ray powder diffractogram having at least three of the reflexes indicated above. Preferably, the crystalline modification I is one having at least four of the aforementioned reflexes, more preferably at least five, six, seven or eight of said reflexes. The crystalline modification I of an embodiment of mesosulfuron-methyl can contain 3 or more of the reflexes indicated above in any combination of reflexes. For example, the crystalline modification I of an embodiment of mesosulfuron-methyl can contain at least reflexes (1), (2), and (3), or at least reflexes (2), (3), and (4), or reflexes (1), (3), and (4), or any other combination of at least three reflexes. An X-ray powder diffractogram of an embodiment of the crystalline modification I of mesosulfuron-methyl is shown in FIG. 2, which will be described in detail hereinafter.

According to a preferred embodiment, the crystalline modification I exhibits at least 3, 4, or 5, or all of the reflexes from the following, again in any combination thereof:

$2\theta=10.88\pm0.2$ (3)

$2\theta=12.14\pm0.2$ (4)

$2\theta=16.38\pm0.2$ (5)

$2\theta=18.87\pm0.2$ (6)

$2\theta=20.82\pm0.2$ (8)

$2\theta=21.88\pm0.2$ (9)

$2\theta=23.22\pm0.2$ (12)

$2\theta=24.50\pm0.2$ (14).

The X-ray powder diffractogram was taken using a diffractometer in reflection geometry in the range from 3°-60° with increments of 0.03° using Cu-Ka radiation at 25° C.

Further to X-ray diffraction analysis, the crystalline modification I of mesosulfuron-methyl according to an embodiment may also be characterized by Infrared (IR) spectroscopy. The IR spectrum of an embodiment of the crystalline modification I is showed in FIG. 1 with characteristic bands at one or more of 3246.88, 2958.83, 1741.75 and 1712.06 cm$^{-1}$.

All IR spectra were obtained using the following acquisition parameters:

| FT-IR spectrometer | Bruker Tensor 37 |
|---|---|
| Diamond ATR unit | from Specac |
| Wavelength range | 550-4000 cm$^{-1}$ |
| Resolution | 4 cm$^{-1}$ |
| Number of scans | 16 |

Figure 3:
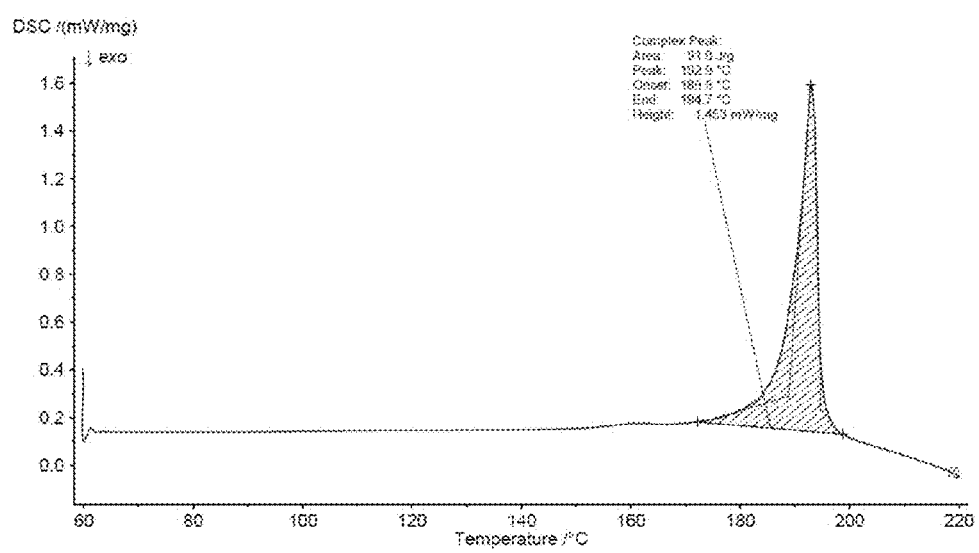
FIG. 3. is a Differential Scanning calorimetry (DSC) spectrum of crystalline modification I of mesosulfuron-methyl, according to an embodiment of the invention.

The crystalline modification I of mesosulfuron-methyl according to the invention may be further characterized by differential scanning calorimetry (DSC) (FIG. 3). An endothermic melting peak with onset at 188.8° C. and peak maximum at about 192.9° C. is shown in FIG. 3. As used herein, the terms "about 192.9° C." means a range of 191° C. to 196° C.

Methods for preparing amorphous mesosulfuron-methyl are well known in the art. Amorphous mesosulfuron-methyl is manufactured and available on a commercial scale. A particularly suitable method for preparing amorphous mesosulfuron-methyl is described in U.S. Pat. No. 5,648,315.

According to an embodiment of the invention, the crystalline modification I of mesosulfuron-methyl can be obtained by the processes below:

Mesosulfuron-methyl in amorphous state is dissolved and then crystallized from solvents.

In one aspect, the invention provides a process for preparing a crystalline modification I of mesosulfuron-methyl comprising steps of:

i) preparing a solution of an amorphous mesosulfuron-methyl in a solvent;

ii) effecting crystallization of mesosulfuron-methyl from the solution to obtain a precipitate; and iii) isolating the precipitated crystalline modification I.

Suitable solvents for mesosulfuron-methyl crystalline modification I include: halogenated hydrocarbons (for example, 1,1-dichloroethane, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions having a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures of any of these.

Preferred solvents include halogenated hydrocarbons, aromatic hydrocarbons (such as benzene, toluene, xylene, chlorobenzene), esters and aliphatic alcohols and mixtures thereof. Particularly preferred solvents or solvent mixtures include 1,1-dichloroethane, toluene, methyl-tetrahydrofuran, diethyl carbonate, chlorobenzene, n-butyl acetate, isobutyl acetate, n-butanol, ethanol, ethyl malonate, methyl t-butyl ether, and their mixtures.

In a particular embodiment of the invention, it is preferred that the solvent is 1,1-dichloroethane, ethanol, or mixture thereof.

Hence, according to a preferred embodiment in step (i), amorphous mesosulfuron-methyl is dissolved in a solvent comprising an ether and/or an alcohol. More preferably, the amorphous mesosulfuron-methyl is dissolved in a solvent comprising 1,1-dichloroethane and/or ethanol (including mixtures thereof).

According to a preferred embodiment in step (i), amorphous mesosulfuron-methyl is dissolved in a solvent or a solvent mixture as a concentrated solution by heating from room temperature or ambient temperature to reflux temperature or below the reflux temperature of the solvent or the solvent mixture. Preferably, the concentrated solutions can be prepared at the reflux temperature of the solvents. The concentration of the solution depends on the solubility of mesosulfuron-methyl in the corresponding solvent or solvent mixture.

In step (ii), mesosulfuron-methyl is crystallized from the solution. Techniques for effecting crystallization of mesosulfuron-methyl from the solution are known to those skilled in the art. For example, in an embodiment where the solution in step (i) is formed at elevated temperatures, crystallization may be effected by cooling the solution to room or ambient temperature, or to a temperature of around 0° C. to 20° C. In one preferred embodiment, crystallization is effected by concentrating the solution formed in step (i) of the process through removing the solvent or solvent mixture to a certain volume either with or without applying vacuum and cooling to below the reflux temperature of the solvent or the solvent mixture.

Alternatively, or in addition thereto, seed crystals, in particular seed crystals of the aforementioned crystalline modification I of mesosulfuron-methyl, may be added to the solution formed in step (i), to facilitate and/or enhance crystallization.

The seed crystal amount added to the concentrated solution is typically in the range of 0.001 to 10% by weight, preferably 0.001 to 2.5% by weight, often 0.005 to 0.5% by weight based on the weight of mesosulfuron-methyl used for the preparation of concentrated solution in step (i). Preferably, the seed crystals are added to the concentrated solution at the temperature below the boiling point of the corresponding solvent or the solvent mixture.

It is preferred that the precipitate of mesosulfuron-methyl recovered during the crystallization stage is washed with a solvent for one or more times. Preferably, the solvent employed in the washing stage consists of one or more components of the solvent employed for forming the solution in step (i), as described hereinbefore. 1,1-dichloroethane and/or ethanol (including mixtures thereof) are particularly suitable solvents for washing the recovered precipitate of mesosulfuron-methyl. The washing is usually carried out using the corresponding solvent or solvent mixture between room temperature and 0° C., depending on the solubility of the crystal, in order to minimize or avoid the loss of crystalline material in the corresponding washing solvent as much as possible.

The invention, in an embodiment, also relates to a composition comprising the crystalline modification I of mesosulfuron-methyl. The amount of the crystalline modification I of mesosulfuron-methyl is desirably less than 75% by weight of the composition, preferably less than 50% by weight of the composition, more preferably less than 30% by weight of the composition, still more preferably about 25% by weight of the composition.

The use of mesosulfuron-methyl, in the amorphous form, as a herbicide is known in the art and is used on a commercial scale. The crystalline modification I of mesosulfuron-methyl is also active in controlling weeds. Techniques of formulating and applying mesosulfuron-methyl in the crystalline modification I are analogous to those known in the art for the amorphous form, for example as disclosed in the prior art documents disclosed hereinbefore. Mesosulfuron-methyl in the crystalline modification I of the present invention may be formulated and applied in an analogous manner to those disclosed in these documents for the amorphous form of mesosulfuron-methyl.

Accordingly, in a further aspect, the invention provides a herbicidal composition comprising mesosulfuron-methyl in the crystalline modification I as defined hereinbefore.

Accordingly, the invention furthermore provides processes for preparing compositions for controlling unwanted plant growth using the crystalline modification I of mesosulfuron-methyl.

Accordingly, the invention also provides a method for controlling unwanted plant growth, comprising applying to the plant, plant part, or surroundings, a herbicidally effective amount of crystalline modification I of mesosulfuron-methyl.

The crystalline modification I of mesosulfuron-methyl can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable herbicidally acceptable auxiliaries, carriers and solvents, in a manner analogous to that known for amorphous mesosulfuron-methyl.

In this context, the crystalline modification I of mesosulfuron-methyl may be present in a concentration sufficient to achieve the required or desired dosage, e.g., in a concentration of from about 0.1% to about 50% by weight of the total mixture. The formulations are prepared, for example, by extending the crystalline modification I of mesosulfuron-methyl with water, solvents and carriers, using, if appropriate, emulsifiers and/or dispersants, and/or other auxiliaries.

These formulations are prepared in a known manner by mixing the crystalline modification I of mesosulfuron-methyl with one or more herbicidally acceptable customary auxiliaries, for example, liquid diluents, solid diluents, wetting agents, dispersants, thickening agents, antifoaming agents and other formulation ingredients.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol, and mixtures thereof. Examples of water-insoluble solid diluents include, but are not limited to, clays, synthetic and diatomaceous silicas, calcium and magnesium silicates, titanium dioxide, aluminium, calcium and zinc oxides, and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Ligninsulfonates such as sodium ligninsulfonates are particularly useful for the composition of the invention. Naphthalene sulfonate-formaldehyde condensates such as naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose and carboxymethylcellulose, and mixtures thereof. Synthetic thickening agents include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention.

Other formulation ingredients can also be used in the present invention such as dyes, drying agents, and the like. These ingredients are known to one skilled in the art.

The crystalline modification I of mesosulfuron-methyl according to an embodiment of the invention can be present in formulations and in its use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as herbicide, the crystalline modification I of mesosulfuron-methyl according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants, plant parts and surroundings thereof can be treated with the crystalline modification I of mesosulfuron-methyl in accordance with an embodiment of the present invention. In the present context, plants are to be understood as meaning all plants and plant populations, such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoots, leaves, needles, stalks, stems, flowers, fruit bodies, fruits, seeds, roots, tubers and rhizomes. Harvested materials, and vegetative and generative propagation materials, for example, cutting, tubers, meristem tissues, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown, or the place on which the plant propagation materials of the plants will be sown, or the environment near the plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment of the plants and plant parts with the compositions or formulations of the inventions according to the invention is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of embodiments of the invention are seen most when the herbicidal composition is applied to kill weeds in growing crops of useful plants: such as maize (corn) including field corns, pop corns and sweet corns, cotton, wheat, barley, rye, triticale, cereals, rice, oats, potatoes, sugar beets, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane. In this invention, cereals and rice are particularly suitable crops for treatment of weeds by the presently disclosed crystalline modification.

All percentages are given in weight % unless otherwise indicated.

Embodiments of the invention will now be described by way of the following examples which are provided for illustrative purposes only, and not intended to limit the scope of the disclosure or the appended claims.

EXAMPLES

Example 1

Preparation of Amorphous Mesosulfuron-Methyl in Accordance with the Disclosure of U.S. Pat. No. 5,648,315

N-tert-Butyl-5-bromomethyl-2-methoxycarbonyl-benzenesulfonamide (Example A1 in U.S. Pat. No. 5,648,315)

A solution of 54.8 g (192 mmol) of N-tert-butyl-2-methoxycarbonyl-5-methylbenzenesulfonamide in 420 ml tetrachloromethane was heated at reflux for 6-8 hours under a nitrogen protective-gas atmosphere, following addition of 36 g (202 mmol) N-bromosuccinimide and 0.5 g azobisisobutyronitrile (AIBN) with simultaneous irradiation with a daylight lamp. The solution was then filtered and then washed in succession with sodium disulphide solution, sodium hydrogen carbonate solution and water, dried over $Na_2SO_4$ and evaporated to dryness under reduced pressure. Crystallization of the residue from diisopropyl ether/ethyl acetate yielded 41.9 g (57%) of N-tert-butyl-5-bromomethyl-2-methoxycarbonylbenzenesulfonamide having melting point of 88° C.-90° C.

N-tert-Butyl-5-azidomethyl-2-methoxycarbonylbenzenesulfonamide (Example A2 in U.S. Pat. No. 5,648,315)

A solution of 25.5 g (70 mmol) N-tert-butyl-5-bromomethyl-2-methoxycarbonylbenzenesulfonamide and 5.9 g (90 mmol) sodium azide in 240 mL of ethanol was heated at reflux for 6 hours. The solution was then evaporated to dryness and the residue was extracted with water/ethyl acetate. Digestion of the crude product with diisopropyl ether gave 16.6 g (72.5%) of N-tert-butyl-5-azidomethyl-2-methoxycarbonylbenzenesulfonamide having melting point of 63° C.-65° C.

N-tert-Butyl-5-aminomethyl-2-methoxycarbonylbenzenesulfonamide (Example A3 in U.S. Pat. No. 5,648,315)

16.3 g (50 mmol) N-tert-butyl-5-azidomethyl-2-methoxycarbonyl benzenesulfonamide were dissolved in 300 ml of methanol and hydrogenated over Pd/C (5%). The mixture was filtered and evaporated to dryness. The crude product obtained was purified by elution through a silica gel column using ethyl acetate/methanol 4:1. 11.2 g (74%) of N-tert-butyl-5-aminomethyl-2-methoxycarbonylbenzenesulfonamide were obtained as a viscous oil.

N-tert-Butyl-5-acetamidomethyl-2-methoxycarbonylbenzenesulfonamide (Example A4 in U.S. Pat. No. 5,648,315)

0.63 g (8 mmol) of acetyl chloride dissolved in 10 ml of dichloromethane was added dropwise to a solution, cooled to 0° C., of 2.01 g (6.7 mmol) of N-tert-butyl-5-aminomethyl-2-methoxycarbonylbenzenesulfonamide and 0.93 ml (6.7 mmol) of triethylamine in 30 ml of dichloromethane, and the mixture was then stirred at room temperature for 2 hours. The reaction solution was washed with water, dried and evaporated to dryness under reduced pressure. 2.1 g (91%) of N-tertbutyl-5-acetamidomethyl-2-methoxycarbonylbenzenesulfonamide are obtained as a viscous oil.

5-Acetamidomethyl-2-methoxycarbonylbenzenesulfonamide (Example A5 in U.S. Pat. No. 5,648,315)

A solution of 2.09 g (6.1 mmol) of N-tert-butyl-5-acetamidomethyl-2-methoxycarbonylbenzenesulfonamide in 25 ml of trifluoroacetic acid was stirred at room temperature for 14 hours and then evaporated to dryness. Crystallization of the residue from ethyl acetate yielded 1.33 g (76%) of 5-acetamidomethyl-2-methoxycarbonyl benzenesulfonamide of melting point of 173° C.-175° C.

Methyl 2-[(4,6-dimethoxypyrimidin-2-ylcarbamoyl) sulfamoyl]-α-(methanesulfonamido)-p-toluate (Example A6 in U.S. Pat. No. 5,648,315)

0.69 g (4.54 mmol) of 1,8-diazabicyclo[5.4.0]undec-7-ene (DBU) was added at 0° C. to a suspension of 1.3 g (4.54 mmol) of 5-acetamidomethyl-2-methoxycarbonyl benzenesulfonamide and 1.25 g (4.54 mmol) of N-4,6-dimethoxypyrimidin-2-yl)phenylcarbamate in 20 ml of acetonitrile. After 2 hours at room temperature, the mixture was diluted with water and diethyl ether, acidified to pH 1-2 with hydrochloric acid, and the resulting precipitate was filtered off and dried. 1.32 g (62%) of methyl 2-[(4,6-dimethoxypyrimidin-2-ylcarbamoyl)sulfamoyl]-α-(methanesulfonamido)-p-toluate having melting point of 149° C.-150° C. were obtained.

Scheme 1. Synthesis of mesosulfuron-methyl

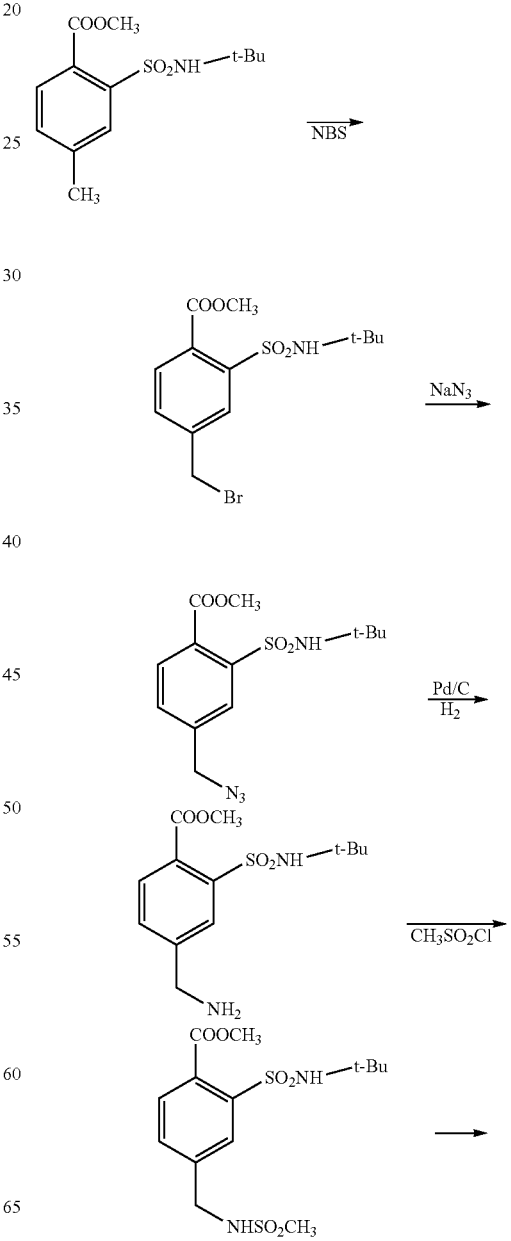

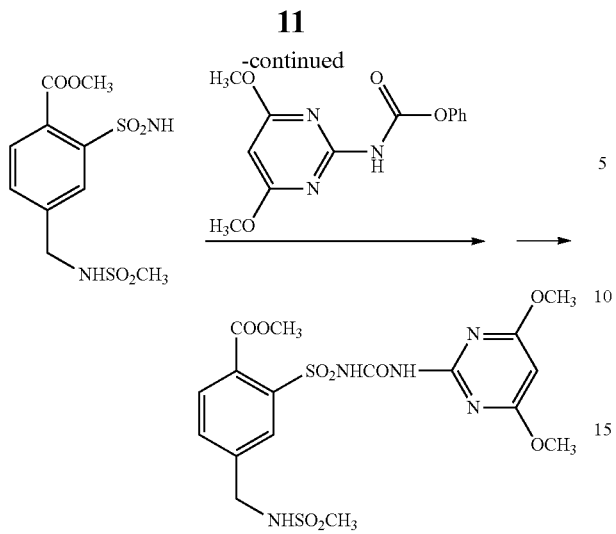

Figure 4:
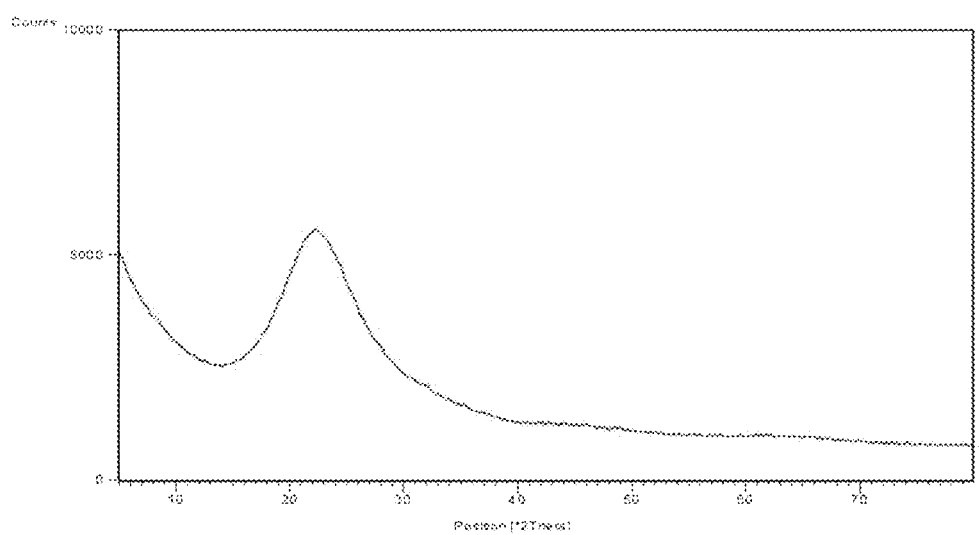
FIG. 4 is a X-ray powder diffractogram of amorphous mesosulfuron-methyl.

As shown in FIG. 4, the X-ray powder diffraction pattern of the resulting mesosulfuron-methyl products prepared above has no significant signals, which indicates the mesosulfuron-methyl product prepared in accordance with the disclosure of U.S. Pat. No. 5,648,315 is amorphous.

Example 2

Preparation of the Crystalline Modification I of Mesosulfuron-Methyl

Crystallization from 1,1-dichloroethane 10 ml 1,1-dichloroethane was charged into the reactor to dissolve crude, amorphous mesosulfuron-methyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with 1,1-dichloroethane. The resulting solid was dried under high vacuum to give crystals of pure mesosulfuron-methyl technical (Purity: 98%).

The crystals were characterized as being of the crystalline modification I of mesosulfuron-methyl using IR spectrometry, X-ray powder diffraction and DSC respectively.

The IR spectrum of the crystalline modification I of mesosulfuron-methyl is set out in FIG. 1. The IR spectrum exhibits characteristic peaks at 3246.88, 2958.83, 1741.75 and 1712.06 cm$^{-1}$.

Differential scanning calorimetry (DSC) (FIG. 3) shows an endothermic melting peak with onset at 188.8° C. and peak maximum at about 192.9° C. in FIG. 3.

The crystalline modification I of mesosulfuron-methyl has the X-ray powder diffractogram shown in FIG. 2 with the reflexes listed in Table 1 below. The X-ray powder diffractogram were taken using a diffractometer in reflection geometry in the range from 3°-60° with increments of 0.03° using Cu-Ka radiation at 25° C.

TABLE 1

| Crystalline modification I | |
|---|---|
| 2 θ (°) | d (Å) |
| 5.41 ± 0.2 | 16.35 ± 0.05 |
| 10.26 ± 0.2 | 8.62 ± 0.05 |

TABLE 1-continued

| Crystalline modification I | |
|---|---|
| 2 θ (°) | d (Å) |
| 10.88 ± 0.2 | 8.13 ± 0.05 |
| 12.14 ± 0.2 | 7.29 ± 0.05 |
| 16.38 ± 0.2 | 5.41 ± 0.05 |
| 18.87 ± 0.2 | 4.70 ± 0.05 |
| 19.47 ± 0.2 | 4.56 ± 0.05 |
| 20.82 ± 0.2 | 4.27 ± 0.05 |
| 21.88 ± 0.2 | 4.06 ± 0.05 |
| 22.55 ± 0.2 | 3.94 ± 0.05 |
| 22.96 ± 0.2 | 3.87 ± 0.05 |
| 23.22 ± 0.2 | 3.83 ± 0.05 |
| 24.10 ± 0.2 | 3.69 ± 0.05 |
| 24.50 ± 0.2 | 3.63 ± 0.05 |
| 26.35 ± 0.2 | 3.38 ± 0.05 |

Example 3

Preparation of the Crystalline Modification I of Mesosulfuron-Methyl

Crystallization from Ethanol 10 mL ethanol was charged into the reactor to dissolve crude, amorphous mesosulfuron-methyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with some ethanol. The resulting solid was dried under high vacuum to give crystals of pure mesosulfuron-methyl technical (Purity: 98%).

The crystals were characterized as being the crystalline modification I of mesosulfuron-methyl using IR spectrometry, X-ray powder diffraction and DSC as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Mesosulfuron-methyl, crystalline modification I, 98% (prepared in Example 2) | 40.8 | 0 | Active compound |
| Amorphous mesosulfuron-methyl (prepared in Example 1) | 0 | 40.8 | Active compound |
| Modified polyether-polysiloxane | 0.5 | 0.5 | Antifoaming agent |
| Ethoxylated castor oil | 15 | 15 | Emulsifier |
| Sodium alkylnaphthalenesulfonate, formaldehyde condensate | 5 | 5 | Dispersing agent |
| Silica | 2 | 2 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Mesosulfuron-methyl, crystalline modification I, 98% (prepared in Example 2) | 25.51 | 0 | Active compound |
| Amorphous mesosulfuron-methyl (prepared in Example 1) | 0 | 25.51 | Active compound |
| Lignosulfonic acid, sodium salt, (REAX ® 88B) | 5 | 5 | Antifoaming agent |
| Sodium lauryl sulfate | 0.5 | 0.5 | Wetting agent |
| Sodium hydrogen carbonate | 2 | 2 | Filler |
| Potassium sulfate | Balance to 100% | Balance to 100% | Carrier |

Example 6

Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Mesosulfuron-methyl, crystalline modification I, 98% (prepared in Example 2) | 25.51 | 0 | Active compound |
| Amorphous mesosulfuron-methyl (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Non-ionic aqueous emulsion of Polydimethylsiloxanes | 1 | 1 | Antifoaming agent |
| Mannitol | Balance to 100% | Balance to 100% | Carrier |

Example 7

Stability Test

The stability of the mesosulfuron-methyl in these compositions was determined by aging samples in heated ovens having the same atmosphere therein, and then comparing the mesosulfuron-methyl content before and after the aging to determine relative percentage of hydrolysis (RPH). RPH was calculated by the following equation:

$$RPH = \frac{\text{(The final weight \% of mesosulfuron-methyl} - \text{The initial weight \% of mesosulfuron-methyl)}}{\text{The initial weight \% of mesosulfuron-methyl}} \times 100\%$$

Mesosulfuron-methyl content was determined by assaying the compositions with high-pressure liquid chromatography (HPLC) using reverse phase columns and eluants.

Samples prepared in Examples 4, 5 and 6 were stored at 54° C. for 1 week. The procedures are followed according to CIPAC MT 46.3. The concentration of mesosulfuron-methyl was measured at the end of each storage time by HPLC. The results are listed in Table 4.

TABLE 4

| Sample | Compound | Weight (%) of mesosulfuron-methyl | RPH % |
|---|---|---|---|
| Example 4 | Mesosulfuron-methyl, crystalline modification I | 40 | 0 |
| | Amorphous mesosulfuron-methyl | 40 | 49 |
| Example 5 | Mesosulfuron-methyl, crystalline modification I, | 25 | 0 |
| | Amorphous mesosulfuron-methyl | 25 | 42 |
| Example 6 | Mesosulfuron-methyl, crystalline modification I, | 25 | 0 |
| | Amorphous mesosulfuron-methyl | 25 | 40 |

The invention claimed is:

1. A crystalline modification I of mesosulfuron-methyl, exhibiting each of the following reflexes as 2θ values in an X-ray powder diffractogram recorded using Cu-Kα radiation at 25° C.:

$2\theta = 5.41 \pm 0.2$ (1)

$2\theta = 10.26 \pm 0.2$ (2)

$2\theta = 10.88 \pm 0.2$ (3)

$2\theta = 12.14 \pm 0.2$ (4)

$2\theta = 16.38 \pm 0.2$ (5)

$2\theta = 18.87 \pm 0.2$ (6)

$2\theta = 19.47 \pm 0.2$ (7)

$2\theta = 20.82 \pm 0.2$ (8)

$2\theta = 21.88 \pm 0.2$ (9)

$2\theta = 22.55 \pm 0.2$ (10)

$2\theta = 22.96 \pm 0.2$ (11)

$2\theta = 23.22 \pm 0.2$ (12)

$2\theta = 24.10 \pm 0.2$ (13)

$2\theta = 24.50 \pm 0.2$ (14)

$2\theta = 26.35 \pm 0.2$ (15).

2. The crystalline modification I of mesosulfuron-methyl according to claim 1, exhibiting a Differential Scanning calorimeter (DSC) thermogram having endothermic melting peak with onset at 188.8° C. and peak maximum at about 192.9° C.

3. The crystalline modification I of mesosulfuron-methyl according to claim 1, exhibiting IR spectrum with the characteristic bands at 3246.88, 2958.83, 1741.75 and 1712.06 cm$^{-1}$.

4. A process for the preparation of a crystalline modification I of mesosulfuron-methyl according to claim 1, comprising:
   i) preparing a solution of an amorphous mesosulfuron-methyl in a solvent, wherein the solvent is 1,1-dichloroethane, ethanol, or a mixture thereof;
   ii) effecting crystallization of mesosulfuron-methyl from the solution to obtain a precipitate; and
   iii) isolating the precipitated crystalline modification I.

5. A composition comprising the crystalline modification I of mesosulfuron-methyl according to claim 1 and at least one herbicidally acceptable auxiliary.

6. The composition according to claim 5, wherein the composition is formulated as a suspension concentrates (SC), an oil-based suspension concentrates (OD), water-soluble granules (SG), a dispersible concentrate (DC), an emulsifiable concentrates (EC), an emulsion seed dressing, a suspension seed dressing, granules (GR), microgranules (MG), a suspoemulsion (SE) or water-dispersible granules (WG).

7. The composition according to claim 6, wherein the composition is formulated as an oil-based suspension concentrate (OD).

8. The composition according to claim 6, wherein the composition is formulated as water-dispersible granules (WG).

9. The composition according to claim 6, wherein the composition is formulated as water-soluble granules (SG).

10. The composition according to claim 5, wherein the auxiliary is selected from the group consisting of one or more of a solvent, a diluent, a wetting agent, a dispersant, a thickening agent and an antifoaming agent.

11. The composition according to claim 5, which comprises crystalline modification I of mesosulfuron-methyl in an amount of less than 75% by weight.

12. A method of controlling undesirable plant growth comprising applying to a plant, plant part, or locus thereof an effective amount of crystalline modification I of mesosulfuron methyl according to claim 1.

* * * * *